(12) United States Patent  (10) Patent No.: US 8,815,529 B2
Wu  (45) Date of Patent: Aug. 26, 2014

(54) SULFOTRANSFERASE ASSAY

(75) Inventor: Zhengliang L. Wu, Edina, MN (US)

(73) Assignee: Research & Diagnostics Systems, Inc., Minneapolis, MN (US)

( * ) Notice: Subject to any disclaimer, the term of this patent is extended or adjusted under 35 U.S.C. 154(b) by 248 days.

(21) Appl. No.: 13/113,637

(22) Filed: May 23, 2011

(65) Prior Publication Data

US 2012/0301909 A1  Nov. 29, 2012

(51) Int. Cl.
*C12Q 1/48* (2006.01)

(52) U.S. Cl.
CPC .................................. *C12Q 1/48* (2013.01)
USPC ........................................... 435/15

(58) Field of Classification Search
USPC ........................................... 435/15
See application file for complete search history.

(56) References Cited

U.S. PATENT DOCUMENTS

| | | | |
|---|---|---|---|
| 7,521,250 B2 | 4/2009 | Hamachi | |
| 7,671,200 B2 * | 3/2010 | Finer et al. | 544/287 |
| 2003/0109501 A1 | 6/2003 | Yang et al. | |
| 2003/0211562 A1 | 11/2003 | Bertozzi et al. | |
| 2008/0233592 A1 | 9/2008 | Lowery | |

FOREIGN PATENT DOCUMENTS

| | | |
|---|---|---|
| EP | 1923402 A1 | 5/2008 |
| WO | 2006017342 A2 | 2/2006 |

OTHER PUBLICATIONS

Vissers et al. [American J. Human Genetics (May 5, 2011, electronic publication).*
Saidha et al. [Biochem. J. (1994), 298: 45-50].*
Fiske & Subbarow [JBC 66 : 375-400 (1925).*
Wu Zhengliang L. et al: "A versatile polyacrylamide gel electrophoresis based sulfotransferase assay", BMC Biotechnology, Biomed Central Ltd., London, GB, vol. 10, No. 1, Feb. 10, 2010, p. 11, XP021067394, ISSN: 1472-6750.
Chen W T et al: "Fluorometric assay for alcohol sulfotransferase", Analytical Biochemistry, Academic Press Inc., New York, vol. 339, No. 1, Apr. 1, 2005, pp. 54-60, XP004781299, ISSN: 0003-2697, DOI: 10.1016/J.AB.2004.12.016.
Johnathan J. Sheng et al: "Measurement of Aryl and Alcohol Sulfotransferase Activity"; "Unit 4.5", In: "Current Protocols in Toxicology", Jan. 1, 2001, John Wiley &U Sons, Inc., Hoboken, NJ, USA, XSP55016337, ISBN: 978-0-47-114085-6, p. 2/9-p. 7/9.
Frederick,et al., "A Role for a Lithium-Inhibited Golgi Nucleotidase in Skeletal Deveopment and Sulfation", Department of Pharmacology and Cancer Biology, Howard Hughes Medical Institute and Department of Psychiatry and Behavioral Sciences, Duke University Medical Center, Durhmam, NC 27710, PNAS, Aug. 19, 2008, vol. 105, No. 33, pp. 11605-11612.
Marion M. Bradford, "A Rapid and Sensitive Method for the Quantitation of Microgram Quantities of Protein Utilizing the Principle of Protein-Dye Binding", Reproduction Research Laboratories, Department of Biochemistry, University of Georgia, Athens, Georgia 30602, Analytical Biochemistry 72, pp. 248-254 (1976).

* cited by examiner

*Primary Examiner* — Tekchand Saidha
(74) *Attorney, Agent, or Firm* — Fredrikson & Byron, PA

(57) ABSTRACT

Assays and methods for detecting and/or quantifying activity of a test sulfotransferase comprising by releasing a free phosphate from the PAP produced by the sulfotransferase reaction and detecting the free phosphate. The assay can includes gPAPP, a free phosphate detector and an optional control sulfotransferase. The method includes combining a test sulfotransferase with the substrate of the sulfotransferase, PAPS and gPAPP and detecting the free phosphate. The level of free phosphate directly correlates to the activity of the sulfotransferase. The assay and methods can be used to screen agents for their effect upon sulfotransferase activity.

9 Claims, 7 Drawing Sheets

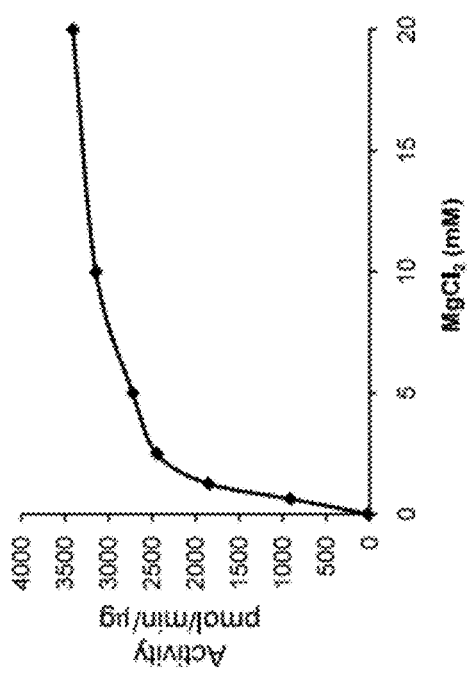
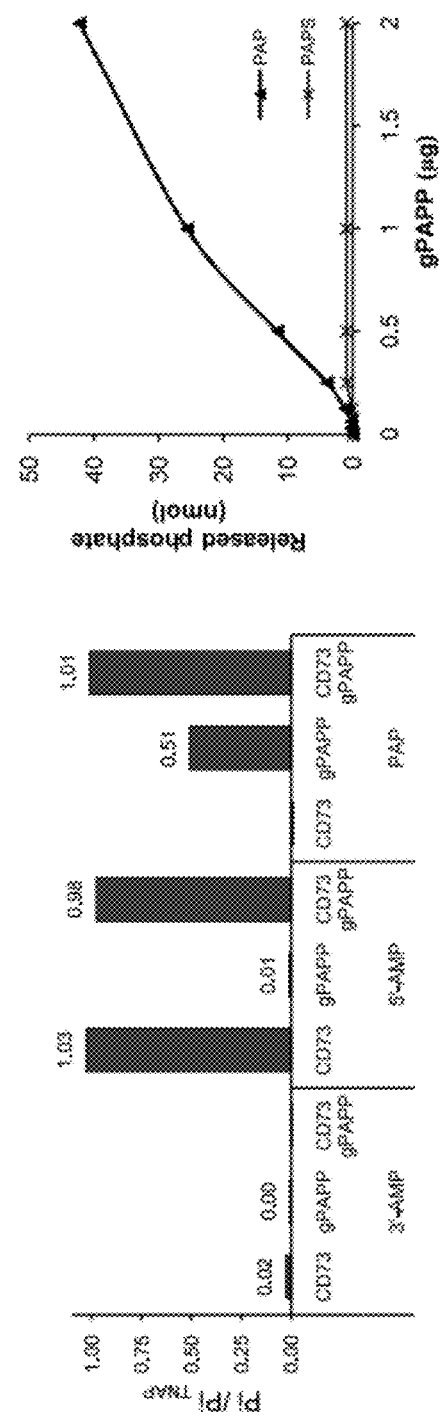
Fig. 4
Fig. 5
Fig. 6

SULFOTRANSFERASE ASSAY

BACKGROUND

Sulfation is a common modification that affects the biological activity of a wide variety of substrates. Sulfation reactions are catalyzed by sulfotransferases. Sulfotransferases are a large group of enzymes that transfer a sulfate from a donor substrate to an acceptor. Many sulfotransferases exist in nature, but in humans, the sulfotransferases are of two types. Cystosolic sulfotransferases (SULTs) are mainly involved in modifying small molecules such as steroids, neurotransmitters, and xenobiotics, and in drug detoxification. Golgi-resident sulfotransferases are involved in modifying glycans and proteins on cell membranes and within the extracellular matrix. Sulfated glycans such as glycosaminoglycans and numerous O- and N-glycans play roles in maintaining biochemical and biophysical properties. Sulfated proteins, such as leukocyte adhesion molecule PSGL-1, play roles in protein-protein and cellular interactions.

Because of the important roles of sulfated molecules in various biological events, sulfotransferases may be ideal targets for drug intervention. Several assays for detecting sulfotransferase activity exist, but they have significant drawbacks. Some sulfotransferase assays uses a radioisotope, $^{35}S$. Such assays require separation steps such as HPLC, TLC, filter blinding, or electrophoresis to separate substrates from products. As such, in addition to the difficulties associated with the use of radioisotopes, the need for separation makes such assays very time consuming. Other methods which can be used include mass spectrometry, fluorescent detection and colorimetric detection. One fluorescent method uses 4-methylumbelliferyl sulfate as the ultimate sulfate donor and measures the fluorescence of 4-methylumbelliferone. Similarly, one colorimetric detection method uses p-nitrophenyl sulfate as the ultimate sulfate donor and measures the color intensity of the generated p-nitrophenol. Each of these methods is either time consuming or lacks efficiency, limiting their usefulness. An assay which can be performed easily and provides results rapidly would be ideal, particularly for screening potential drugs for their effect on sulfotransferases.

SUMMARY

Embodiments of the invention include assays, methods and kits for detecting and quantifying sulfotransferase activity. Embodiments of the invention use a phosphatase, Golgi-resident PAP-specific 3'-phosphatase (gPAPP), which selectively removes a phosphate from the 3'-phosphoadenosine-5'-phosphate (PAP) produced by the sulfotransferase reaction. The free phosphate released by gPAPP can then be detected and quantified, with the amount of free phosphate correlating to the activity of the sulfotransferase.

In one embodiment, an assay for detecting activity of a sulfotransferase of interest, which can be referred to as a test sulfotransferase, includes gPAPP and a free phosphate detector. The free phosphate detector may be a colorimetric assay. In some embodiments, the free phosphate detector includes a first reagent including ammonium molybdate and the second reagent including malachite green oxalate. The assay may further include a control sulfotransferase such as SULT1C4 or CHST3. The assay may also include a free phosphate standard. The assay may also include 3'-phosphoadenosine-5'-phosphosulfate (PAPS) and/or PAP. In some embodiments, the assay includes a buffer, which may include magnesium.

In another embodiment, an assay for detecting activity of a test sulfotransferase includes gPAPP, a 5' nucleotidase, and a free phosphate detector. The assay may further include PAPS and/or PAP. In some embodiments, the assay also includes a control sulfotransferase.

Embodiments of the invention also include methods for detecting and/or quantifying sulfotransferase activity. In one embodiment, the method includes combining a sulfotransferase, gPAPP, a substrate of the sulfotransferase, and PAPS under conditions to produce PAP as a first reaction, and measuring free phosphate. The method may further include calculating sulfotransferase activity using the measured amount of free phosphate. In some embodiments, measuring the free phosphate include measuring optical density. In some embodiments, the method further includes conducting a second reaction, including combining the substrate of the sulfotransferase and PAPS with gPAPP in the absence of the sulfotransferase and measuring free phosphate, wherein the second reaction provides a background control for the first reaction (which included the sulfotransferase). For example, the method can include reducing the measured phosphate of the first reaction by the measured phosphate of the second reaction to calculate the amount of phosphate resulting from the sulfotransferase reaction.

In some embodiments, measuring free phosphate includes applying a colorimetric free phosphate detection assay to the first reaction. In some such reactions, measuring free phosphate includes adding a first reagent including ammonium molybdate to the reaction, and then adding a second reagent including malachite green oxalate to the reaction.

In other embodiments, a method of detecting sulfotransferase activity includes conducting a first reaction comprising combining a sulfotransferase, gPAPP, a 5'-nucleotidase, a substrate of the sulfotransferase, and PAPS under conditions to produce PAP and measuring free phosphate.

FIGURES

FIG. 4 is a graph of gPAPP activity versus $MgCl_2$ concentration;

FIG. 5 is a graph of the ratio of free phosphate released by gPAPP and/or CD73 (Pi) to the free phosphate released by TNAP ($Pi_{TNAP}$) from 3'-AMP, 5'-AMP and PAP;

FIG. 6 is a graph of phosphate released from PAPS and PAP versus gPAPP concentration;

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Embodiments of the invention provide methods and assays for quickly and easily detecting and quantifying the activity of sulfotransferase enzymes. Embodiments of the invention are useful for high throughput testing of drugs to evaluate their effect upon sulfotransferases.

Embodiments of the invention utilize the nearly universal use of PAPS as the sulfate donor in sulfotransferase reactions, with ultimate release and detection of the phosphate in the PAPS using a colorimetric assay.

Figure 1:
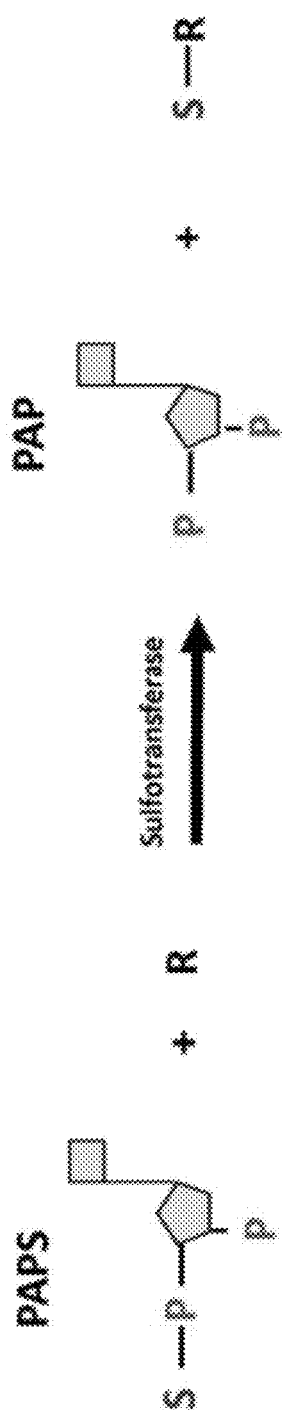
FIG. 1 is a representative sulfotransferase reaction.

To better understand the embodiments of the invention, a generic sulfation reaction is shown in FIG. 1. The substrate is shown as R. After sulfation by the sulfotransferase, the sulfated product is shown as S—R. In nearly all sulfation reactions, the sulfate donor is PAPS, and this sulfate donor is shown. After the transfer of the sulfate to the substrate S, it can be seen that the PAPS looses its sulfate and becomes PAP. Each sulfation reaction therefore results in the production of 1 molecule of PAP. Embodiments of the invention rely upon this one to one nature of the relationship between PAP production and sulfation, and the nearly universal nature of PAPS as the sulfate donor, to provide a method to detect and quantify sulfation as further described below. It can also be seen that the removal of the sulfate from PAPS results in the exposure of the 3' phosphate of PAP, which makes the 3' phosphate available for release by a gPAPP.

Figure 2:
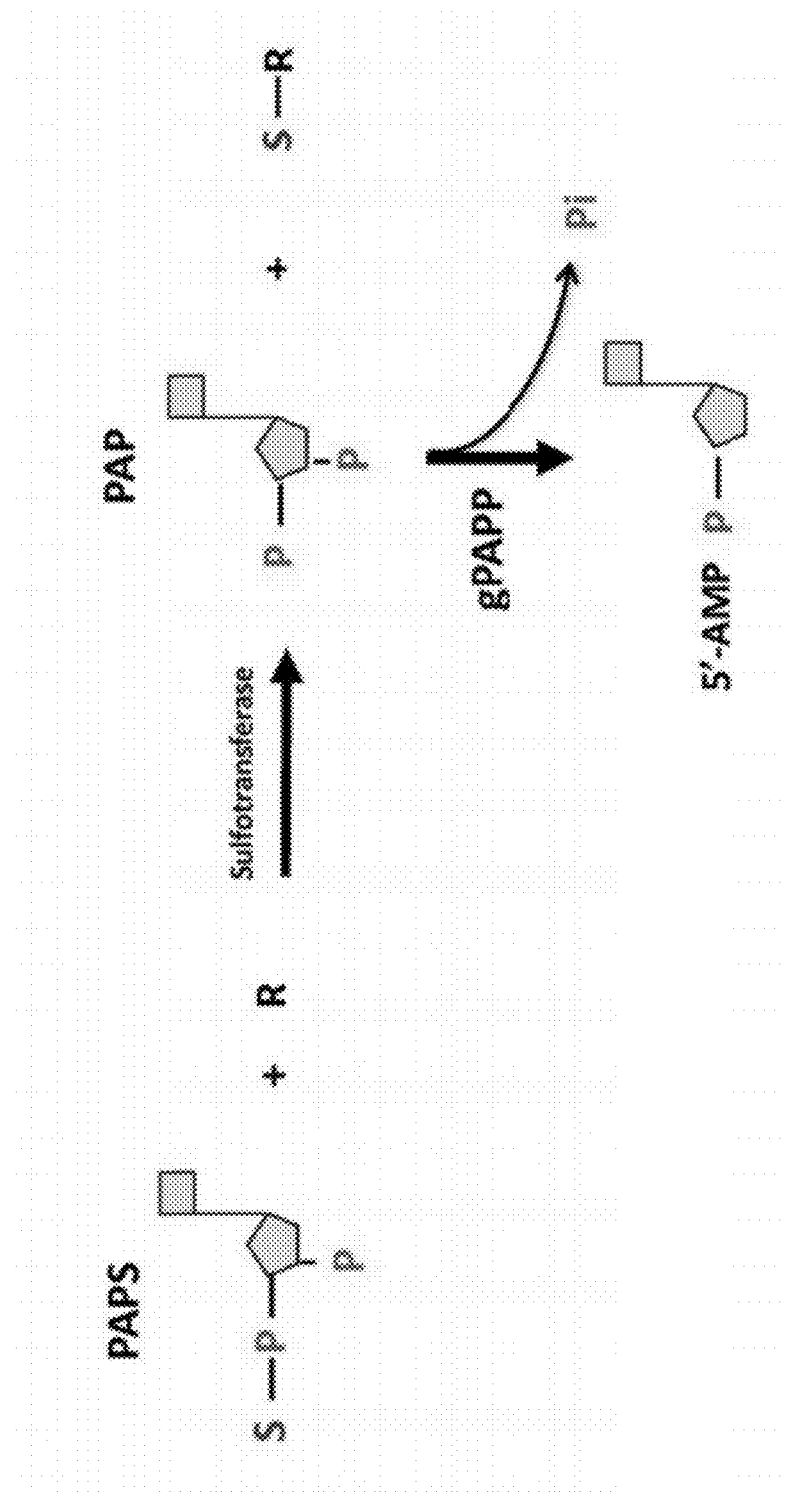
FIG. 2 is a sulfotransferase reaction including release of free phosphate according to embodiments of the invention.

FIG. 2 shows how embodiments of the invention can be used to assay sulfotransferase activity by utilizing the production of PAP from PAPS. The sulfotransferase reaction proceeds as shown in FIG. 1, with the production of PAP in direct correlation to sulfotransferase activity. The PAP then reacts with a PAP specific phosphatase, gPAPP, to release the 3' phosphate from the PAP and generate 1 molecule of 5-adenosine monophosphate (5'-AMP) and one molecule of free phosphate. The quantity of the free phosphate produced can then be detected by one of various known free phosphate detectors, and this amount directly correlates to the activity of the sulfotransferase. In some embodiments, the free phosphate detector is a colorimetric assay, which is particularly useful for high throughput testing.

Embodiments of the invention may be used with any sulfotransferase which uses PAPS as the sulfate donor. This includes nearly all known sulfotransferases, including all human and all other mammalian sulfotransferases and some bacterial sulfotransferases. Indeed, all sulfotransferases, except for a small number present in bacteria, use PAPS as the sulfate donor. Examples of specific sulfotransferases which can be used in embodiments of the invention include carbohydrate sulfotransferases (such as CHST1, CHST2, CHST3, CHST4, CHST5, CHST6, CHST7, CHST8, CHST9, CHST10, CHST11, CHST12, CHS13, CHS14 and CHS15), galactose-3-o-sulfotransferases (such as GAL3ST1, GAL3ST2, GAL3ST3, and GAL3ST4), heparin sulfate 2-O-sulfotransferases (such as HS2ST1), heparin sulfate 3-O-sulfotransferases (such as HS3ST1, HS3ST2, HS3ST3A1, HSEST3A2, HS3ST3B1, HS3ST3B2, HS3ST4, HS3ST5, and HS3ST6), heparin sulfate 6-O-sulfotransferases (such as HS6ST1, HS6ST2, and HS6ST3), N-deacetylase/N-sulfotransferases (such as NDST1, NDST2, NDST3, and NDST4), tyrosylprotein sulfotransferases (such as TPST1 and TPST2), uronyl-2-sulfotransferases (such as UST), estrone sulfotransferases, chondroitin 4-sulfotransferases, and others, such as SULT1A1, SULT1A2, SULT1A3, SULT1B1, SULT1C3, SULT1C4, SULT1DP, SULT1E1, SULT2A1, SULT2B1, SULT4A1 and SULT6B1. Embodiments of the invention can also be used with microbial sulfotransferases, such as Nod factor H, a sulfotransferase of *Rhizobium melioti* involved in establishing nitrogen-fixing symbiosis between rhizobia and leguminous plants, and StaL, a glycopeptide antibiotic sulfotransferase from *Streptomyces toyocaensis*.

The substrate used in embodiments of the invention is any substrate which is acted upon by the sulfotransferase used in the assay. The substrate may be a protein, carbohydrate, lipid or steroid, for example. Other examples of substrates include peptides, oligosaccharides, drugs and xenobiotics. For example, sulfation by cytosolic sulfotransferases can be one step in the metabolism of certain drugs or xenobiotics. Therefore in some embodiments, a drug or xenobiotic may be used as a substrate and the assay may be used to analyze the rate of sulfation of the drug or xenobiotic. In some embodiments, a drug or xenobiotic may be used as a substrate and an additional agent may be added to the reaction, such as a potential promoter or inhibitor of the sulfotransferase, to determine the effect of the additional agent upon the metabolism of the drug or xenobiotic by the sulfotransferase.

Embodiments of the invention take advantage of the specificity of gPAPP as a coupling phosphatase. Both PAP and PAPS include phosphate moieties that could be removed by phosphatases. However, gPAPP is specifically active on PAP and not on PAPS. As such, all phosphate released by gPAPP is from PAP and not from PAPS. Because PAP is produced by the sulfotransferase reaction, the production of PAP directly correlates to the activity of the sulfotransferase. The specificity of gPAPP therefore allows phosphate to be released from PAP only, and this phosphate can then be measured, such that the measured amount of phosphate directly correlates to the activity of the sulfotransferase.

The phosphatase gPAPP may be isolated from naturally occurring sources or may be produced recombinantly. The phosphatase gPAPP useful in embodiments of the invention also include any homologue proteins from different organisms and any mutational variations described herein. On method of obtaining gPAPP which may be used in embodiments of the invention is by using recombinant mouse gPAPP from E51 to K356 (Gene ID: 242291) which can be expressed in CHO cells as an N-terminal His-tagged recombinant protein and purified using nickel affinity resin and Superdex-200 from GE Healthcare (Pittsburgh, Pa.). Further description of how to make gPAPP which can be used in embodiments of the invention can be found in Frederick, J. P., et al. (2008) *A role for a lithium-inhibited Golgi nucleotidase in skeletal development and sulfation. Proc Natl Acad Sci USA.* 105, 11605-11612, the relevant portions of which are hereby incorporated by reference. One method of obtaining PAPS which can be used in embodiments of the invention it by using recombinant *S. cerevisiae* ATP sulfurylase and *P. chrysogenum* APS kinase, then purifying the PAPS using a DEAE Sepharose fast-flow column from GE Healthcare, for example. Further description of how to produce PAPS which may be used in embodiments of the invention is provided in Wu, Z. L., et al. *A versatile polyacrylamide gel electrophoresis based sulfotransferase assay. BMC biotechnology.* 10,11, the relevant portions of which are hereby incorporated by reference.

Some embodiments include the use of PAP, such as including PAP as a component of the assay. PAP which can be used in embodiments of the invention is commercially available from Sigma Aldrich (St Louis, Mo.). After release of the phosphate from the PAP by gPAPP, the free phosphate may be readily detected and/or measured by any means. Several methods are known for measuring free phosphate, any of which may be used. In some embodiments, the free phosphate may be detected and/or measured using a colorimetric assay. Examples of colorimetric assays for measurement of free phosphate which may be used in embodiments of the invention include the Malachite Green Phosphate Detection Kit available from R & D Systems, (Minneapolis, Minn.), PiColorlock™ Assay reagent available from Innova Biosciences, Ltd. (Cambridge, U.K.), and Phosphate Colorimetric Assay Kit available from BioVision (Mountain View, Calif.). In other embodiments, the free phosphate may be detected and/or measured by fluorescence detection. For example, free phosphate may be selectively detected by a fluorescent sensor as described in U.S. Pat. No. 7,521,250, the disclosure of which is hereby incorporated by reference. In another example, free phosphate may be detected using a recombinant E. coli phosphate-binding protein labeled with the fluorophore MDCC known as Phosphate Sensor and available from Invitrogen (Carlsbad, Calif.).

The Malachite Green Phosphate Detection Kit is one method that may be used to detect free phosphate and is based on the malachite green-molybdate binding reaction, and the kit itself, or the components or variations thereof, may be used in embodiments of the invention. The Malachite Green assay includes a first reagent, Malachite Green Reagent A, which includes ammonium molybdate and sulfuric acid, and a second reagent, Malachite Green Reagent B, which includes malachite green oxalate and polyvinyl alcohol. The Malachite Green assay further includes a phosphate standard, $KH_2PO_4$. The phosphate standard may be used to create a standard curve of absorbance at 620 nm for interpretation of sample assay results. The use of the assay includes incubating a sample with Malachite Green Reagent A for 10 minutes at room temperature, then adding Malachite Green Reagent B and incubating for 20 minutes at room temperature. The absorbance may then be read at 620 nm and compared to the phosphate standard curve to determine the amount of phosphate present in the sample.

The Malachite Green Phosphate Detection kit itself, or components or variations thereof, may therefore be used to detect levels of free phosphate released from PAP, according to embodiments of the invention. In such embodiments, PAPS, substrate, sulfotransferase, assay buffer, and gPAPP are combined to produce a sample for testing. In some embodiments, the sample may further include an additional component or test agent, such as a potential sulfotransferase inhibitor or promoter. At the completion of the reaction time, the resulting sample may be combined with Malachite Green Reagent A to stop the reaction, then incubated 10 minutes, and then combined with Malachite Green Reagent B and incubated an additional 20 minutes as described above. The absorbance may then be read at 620 nm using a spectrometer, and the reading may be correlated to a phosphate standard curve and/or a control (including all reaction components except the sulfotransferase enzyme), to determine the amount of free phosphate released by gPAPP. This amount may be compared to the initial quantity of PAPS and/or sulfotransferase present in the sample to determine the activity of the sulfotransferase. When a test agent is used, this amount may be compared to the amount of phosphate produced in a reaction including all of the same components except the test agent, to determine the effect of the test agent upon the sulfotransferase activity.

It should be noted that the PAP produced by the sulfatase reaction includes two phosphate molecules, which are known as the 3' and 5' phosphates. The phosphatase gPAPP is not only specific for PAP (as compared to PAPS) but also is specific for the 3' phosphate of PAP, such that gPAPP only releases the 3' phosphate from PAP while the 5' phosphate is unaffected. In the reaction shown in FIG. 2, the 5' phosphate remains bound to the PAP and is not detected by the free phosphate detector. However, in some embodiments, the 5' phosphate can also be removed from PAP through the use of an additional specific phosphatase (a 5'-nucleotidase).

Figure 3:
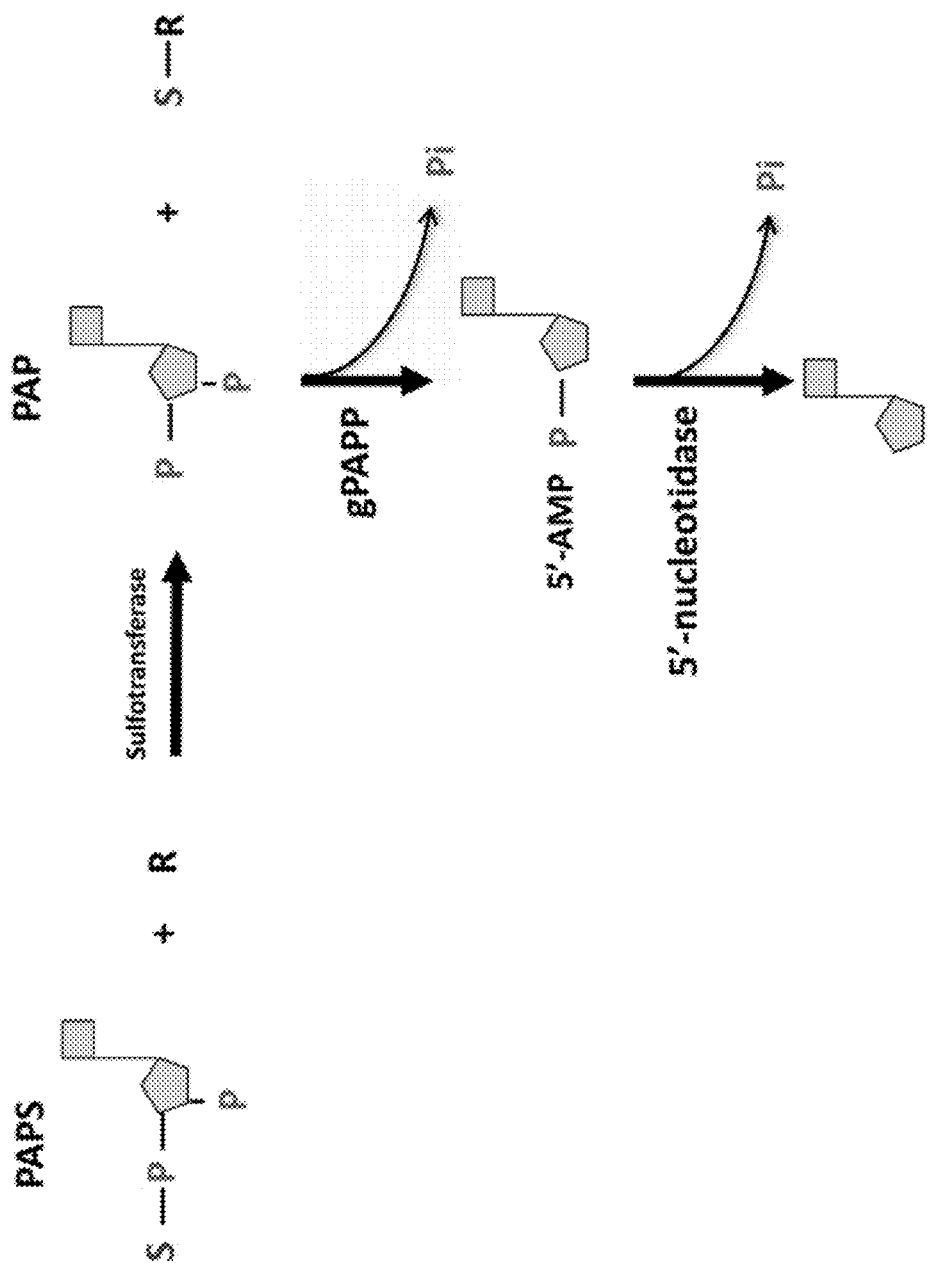
FIG. 3 is another sulfotransferase reaction including release of free phosphate according to embodiments of the invention.

An example of a reaction in which two phosphates are released is shown in FIG. 3. The first portion of this reaction is the same as the reaction shown in FIG. 2, with PAPS converted to PAP during the sulfotransferase reaction, and gPAPP releasing one phosphate (the 3' phosphate) from each PAP produced. Removal of the 3' phosphate from PAP produces 5'-AMP. In this embodiment, the reaction also includes a 5'-nucleotidase which removes the remaining phosphate from 5'AMP to produce an additional molecule of phosphate and an adenosine for each sulfotransferase reaction.

Examples of 5'-nucleotidases which may be used in embodiments of the invention include CD73, NT5DC1, NT5DC2, NT5DC3, cytosolic 5'-nucleotidase IA (NT5C1A), cytosolic 5'-nucleotidase IB (NT5C1B), cytosolic 5'-nucleotidase II (NT5C2), cytosolic 5'-nucleotidase III (NT5C3), NT5C3L, NT5DC4. The 5'-nucleotidases may be isolated from naturally occurring sources or may be produced recombinantly and many are commercially available. The 5'-nucleotidases useful in embodiments of the invention also include any homologue proteins from different organisms and any mutational variations of any of the phosphatases described herein.

PAP has been reported to be a potent inhibitor of sulfotransferases and as such has the potential to inhibit the same reaction which is being assayed and in which it is produced. This aspect of sulfotransferase reactions makes development of an assay more complicated. However, because embodiments of the invention promptly degrade PAP to 5'-AMP using gPAPP, this potential inhibition does not occur. As such, in addition to providing a way to detect and quantify sulfotransferase reactions, embodiments of the invention avoid the inhibition of sulfotransferase reactions which can be caused by the production of PAP.

Embodiments of the invention include assays, kits and methods for detecting and measuring sulfotransferase activity. In some embodiments, the assay includes one or more of the following components: PAPS; gPAPP; a buffer; and a control sulfotransferase. The assay may optionally include free phosphate detection reagents, such as a first reagent comprising molybdate and a second reagent comprising malachite green. In some embodiments, the assay may also include PAP.

In some embodiments, the kit may include gPAPP and a free phosphate detection assay. In other embodiments, the kit may include PAPS and gPAPP. In still other embodiments, the kit may include gPAPP, a free phosphate detection assay, and PAPS. The kit may further include an assay buffer, PAP and/or a phosphate standard. The phosphate detection assay may be a Malachite Green detection assay. The PAPS and/or PAP may be supplied in the assay buffer. The gPAPP may also be supplied in the assay buffer.

In one embodiment, the sulfotransferase assay kit includes an assay buffer, gPAPP, PAPS, Malachite Green Reagent A, Malachite Green Reagent B, and a phosphate standard, such as $KH_2PO_4$. The kit may further include a sulfotransferase to be used as a positive control for the various components of the kit. The gPAPP, PAPS and/or the control sulfotransferase may be provided in the assay buffer. In some embodiments, the kit further includes a 5'-nucleotidase.

A sulfotransferase may be provided as a control in the kit, or a control sulfotransferase may be supplied by the user of the kit. The control sulfotransferase serves to assure proper functioning of the assay. The assay may be performed using the control sulfotransferase and the results may be compared to known expected results for the sulfotransferase. If the results are within the expected range, the assay can be considered to be functioning properly. In this way, when the assay is performed using a sulfotransferase of interest, the results may be considered reliable. A control sulfotransferase provided in a kit is preferably stable over time and has a known activity, and the data regarding the control sulfotransferase activity and expected results may be provided with the kit. Examples of sulfotransferases which may be provided in kits to serve as controls include any stable sulfotransferase having a high specific activity and an available substrate, such as SULT1C4 and CHST3.

The use of the kit may include first creating a free phosphate standard curve. For colorimetric assays, the phosphate standard curve may be created using serial dilution of a phosphate standard in the assay buffer, and followed by measuring the absorbance using a phosphate detection reagents. For example, each dilution may be combined with Malachite Green Reagent A and then with Malachite Green Reagent B as described and the absorbance may be read at 620 nm. The resulting measurements may be used to create a phosphate standard curve which may be used to calculate the phosphate conversion factor, the amount of phosphate corresponding to a unit of absorbance.

In order to correlate assay results to levels of free phosphate, and thereby to sulfotransferase activity, a phosphate standard curve may be produced. In embodiments in which a Malachite Green assay is used to measure free phosphate, and in embodiments using other free phosphate detection methods as well, the phosphate standard curve may be made using serial dilutions, such as 2-fold serial dilutions, of a phosphate solution such as the phosphate standard, in the assay buffer. For example, the serial dilutions may be as in Table 1, below.

TABLE 1

| Well | Phosphate concentration (µm) | Phosphate input (nmole) |
|---|---|---|
| 1 | 50 | 5,000 |
| 2 | 25 | 2,500 |
| 3 | 12.5 | 1,250 |
| 4 | 6.25 | 625 |
| 5 | 3.13 | 313 |
| 6 | 1.56 | 156 |
| 7 | 0.78 | 78 |
| 8 | 0 | 0 |

When the Malachite Green assay is used, for example, the serial phosphate dilutions may be added to a clear 96-well plate and may be performed in triplicate. The Malachite Green Reagent A is first added to each well, followed by the Malachite Green Reagent B. After 20 minutes, the optical density (OD) is read at 620 nm for each well using a microplate reader or spectrophotometer. The average OD for each dilution may be obtained. The phosphate input may be plotted against the OD, or the average of the OD for each dilution, to create a standard curve, such as by using linear regression or a computer generated four parameter logistic (4-PL) curve fit. A similar curve may be obtained using other free phosphate detection methods or other phosphate sources. The slope of the linear regression line may be used as the conversion factor, i.e. the amount of phosphate corresponds to an absorbance unit. This conversion factor may then be used to calculate the amount of free phosphate from the measured absorbance for each reaction.

In some embodiments, a single buffer is used which is the assay buffer. The assay buffer should allow the sulfotransferase, and preferably also gPAPP and the 5'-nucleotidase, if used, to function normally. In some embodiments, the assay buffer may contain about 10 mM $MgCl_2$ and may have a pH of about 7.0 to about 8.0. In some embodiments, the assay buffer may comprise 25 mM Tris and 10 mM $MgCl_2$ at pH 7.5. In other embodiments, two or more buffers may be used. The first buffer may be an assay buffer and the second buffer may be a phosphatase buffer. For example, the phosphatase may be $Mg^{2+}$ dependent, and therefore the phosphatase buffer should include $Mg^{2+}$, while the assay buffer might not have this component.

In some embodiments, the buffer and other reagents have divalent cations such as calcium, magnesium and manganese. In some embodiments, gPAPP (and the 5'-nucleotidase, if used) may be active in the assay buffer used with or provided with the assay. In such embodiments, gPAPP may be combined with the PAPS, the substrate, and the sulfotransferase, in the same buffer. In other embodiments, gPAPP is not active in the assay buffer used with or provided with the assay. In such embodiments, PAPS, the substrate, and the sulfotransferase may first be combined in a first buffer which is the assay buffer and allowed to react. A second buffer which is the gPAPP buffer may then be added after the completion of the first reaction. The gPAPP may be added with the gPAPP buffer or may be added after the addition of a sufficient amount of the gPAPP buffer. The gPAPP buffer may be stronger than the sulfotransferase assay buffer, such that the conditions provided by the gPAPP buffer will overwhelm those provided by the assay buffer, with the resulting mixture being more similar to the gPAPP buffer and therefore being favorable for gPAPP activity.

Embodiments of the invention provide convenient ways to detect and quantify sulfotransferase activity. The assays described herein do not involve radioisotope usage and do not require chemical separation, like previous methods. Furthermore, the assays described herein can be performed using multi-well high throughput techniques.

Embodiments of the invention further include methods of detecting and/or quantifying the activity of a sulfotransferase. In some embodiments, the method includes performing a first reaction including combining a sulfotransferase, which may be considered a test sulfotransferase, with a substrate of the sulfotransferase and PAPS in a reaction buffer. The method further includes combining the reactants with gPAPP. In some embodiments, the gPAPP may be combined simultaneously or approximately simultaneously with the other reactant. In other embodiments, the sulfotransferase, substrate and PAPS are combined first and allowed to react, and then the gPAPP is added to the reaction after the reaction has progressed for a certain amount of time, such as about 20 minutes.

In some embodiments, the method includes performing a first reaction including combining a sulfotransferase which is a test sulfotransferase with a substrate of the sulfotransferases and PAPS in a reaction buffer. The method further includes combining the reactants with gPAPP and a 5'-nucleotidase. In some embodiments, the gPAPP and the 5'-nucleotidase may be combined simultaneously or approximately simultaneously with the other reactants. In other embodiments, the gPAPP and the 5' nucleotidase are combined with the other reactants after the sulfotransferase reaction has progressed for a certain amount of time, such as about 20 minutes. In still other embodiments, the gPAPP is added to the reaction first either simultaneously or after allowing the sulfotransferase reaction to progress and then the 5'-nucleotidase is added after allowing time for the gPAPP to react.

The next step in any of the embodiment is measuring the level of free phosphate. In some embodiments, the reaction is tested using a free phosphate detector such as the Malachite Green assay as described above. In such embodiments, malachite reagent A is added first, followed by the addition of malachite reagent B.

In any of the methods described above, measuring the level of free phosphate may include measuring OD and comparing the measured OD to a free phosphate standard curve or applying a conversion factor which may be determined using a free phosphate standard curve to the measured OD, to convert the measured OD to a free phosphate level. In such embodiments, the method may further include preparing the free phosphate standard curve.

In any of the methods described above, the method may further include performing a second reaction which is a control reaction. In some embodiments, performing the control reaction includes combining each of the reactants as in the first reaction (the test reaction) in the same manner and under the same conditions as the test reaction but in the absence of the sulfotransferase. For example, performing the second reaction may include combining the substrate of the sulfotransferase with PAPS, and either concurrently or subsequently adding gPAPP, depending upon how the test reaction was performed. If used in the test reaction, the 5'-nucleotidase would also be combined with the reactants, in the same manner as in the test reaction. The method further includes measuring the level of free phosphate in the second reaction, and this step would be performed in the same manner as in the test reaction. Finally, the method may include subtracting the measured free phosphate of the second reaction from the measured free phosphate of the first reaction. In this way, the results can be adjusted to compensate for any free phosphate, PAP and 5'-AMP that may be present in the reagents and are not caused by the sulfotransferase reaction. For example, some amount of PAPS may spontaneously degrade to PAP even in the absence of a sulfotransferase, making the PAP available to the gPAPP and resulting in some amount of free phosphate. By adjusting (reducing) the level of the free phosphate measured in the sulfotransferase test reaction by the amount of free phosphate present in the control, a more accurate measurement of sulfotransferase activity can be obtained which does not depend upon the stability of PAPS.

In some embodiments, the assay is used to evaluate the effect of a test agent on the sulfotransferase. In such embodiments, the sulfotransferase, substrate, PAPS and test agent are combined in a test reaction, and gPAPP may be added simultaneously or subsequently. In some embodiments, a 5' nucleotide may also be added to the reaction. Next the phosphate level is measured as in the other methods. The phosphate level (or the activity of the sulfotransferase which may be determined using the phosphate level) is compared to the phosphate level (or sulfotransferase activity) for a separate reaction (a control reaction) including the same reactants but without the test agent. The control reaction may either be performed or its values (phosphate level and/or sulfotransferase activity) may already be known and used for comparison to the test reaction.

EXAMPLES

In the following examples, the gPAPP used was recombinant mouse gPAPP expressed in CHO cells as an N-terminal His-tagged recombinant protein containing amino acids from E51 to K356, created by R & D Systems. The sequence was based on accession number NP 808398 from the National Center for Biotechnology Information. The chondroitin sulfate (CS) and p-nitrophenol (pNP) were obtained from Sigma Aldrich. The PAPS was prepared by R & D Systems using recombinant *S. cerevisiae* ATP sulurylase and *P. chrysogenum* APS kinase. The APS kinase was also prepared by R & D Systems. Recombinant human SULT1A1, CHST3, CD73, TNAP and Malachite Green Phosphate Detection Kit were from R & D Systems. Protein concentrations were quantified using the Bradford assay as described by Bradford, M. M., *A rapid and sensitive method for the quantitation of microgram quantities of protein utilizing the principle of protein-dye binding. Anal Biochem.* 1976. Vol 72, Page 248-254, the relevant portions of which are hereby incorporated by reference. Phosphate levels were determined using the Malachite Green Phosphate Detection Kit available from R & D Systems, according to the package instructions. All examples were performed in a buffer of 25 mM Tris at pH 7.5.

Example 1

First, the activity of gPAPP in the presence of $Mg^{2+}$ was tested by combining 0.025 µg gPAPP, 25 nmol PAP and increasing amounts of $Mg^{2+}$ in 50 µL of assay buffer of 25 mM Tris at pH 7.5. The results are shown in FIG. 4. As can be seen, gPAPP was found to be active in the presence of $Mg^{2+}$, and a maximum activity was achieved when the $Mg^{2+}$ concentration was greater than 10 mM. The magnesium dependence of gPAPP is consistent with its localization in the Golgi apparatus and the presence of magnesium transporters in the Golgi apparatus. In a second experiment, the activity of gPAPP was evaluated at various pH levels. The activity of gPAPP in the presence of 10 mM $Mg^2$ was tested by combining 0.025 µg gPAPP, 25 nmol PAP in 50 µL of buffers at different pH levels. It was found that gPAPP was active at a pH from 4.0 to 9.0, with optimal activity around pH 7.5.

Example 2

The specificity of gPAPP was first tested on 3'-AMP, 5'-AMP and PAP in the absence or presence of CD73 by combining 10 nmol of either 3'-AMP, 5'-AMP or PAP with 1 µg gPAPP and/or 0.1 µg CD73 in 50 µL assay buffer containing 10 mM $Mg^2$ at pH 7.5. In a parallel experiment, the same amount of nucleotide was combined with tissue-non-specific alkaline phosphatase (TNAP) at pH 9.0. The ratio between the phosphate released by gPAPP and/or CD73 (Pi) and the phosphate released by TNAP ($Pi_{TNAP}$) was plotted versus the nucleotide and phosphatases in FIG. 5. It can be seen that gPAPP alone showed activity on PAP but not 3'-AMP or 5'-AMP. When gPAPP and CD73 were used together, they released twice as much phosphate from PAP than gPAPP alone. These results confirmed that gPAPP is a PAP-specific 3'-nucleotidase and CD73 is a 5'-nucleotidase.

Example 3

The specificity of gPAPP was tested on PAP and PAPS. These results are shown in FIG. 6. In this example, 50 nmol of either PAP or PAPS was treated with different amounts of gPAPP in 50 µL assay buffer containing 10 mM $Mg^2$ at pH 7.5 for 20 minutes. The released phosphate was plotted versus the amount of gPAPP. While the phosphate released from PAP by gPAPP increased with the amount of the enzyme, the phosphate released from PAPS by gPAPP showed no change. The results of examples 1-3 demonstrate that gPAPP can be used as a coupling phosphatase in sulfotransferase assays to release the 3'-phosphate from PAP, and that CD73 can be used as a secondary coupling phosphatase to further release the 5'-phosphate from 5'-AMP produced in a gPAPP-coupled sulfotransferase reaction.

Example 4

Figure 7:
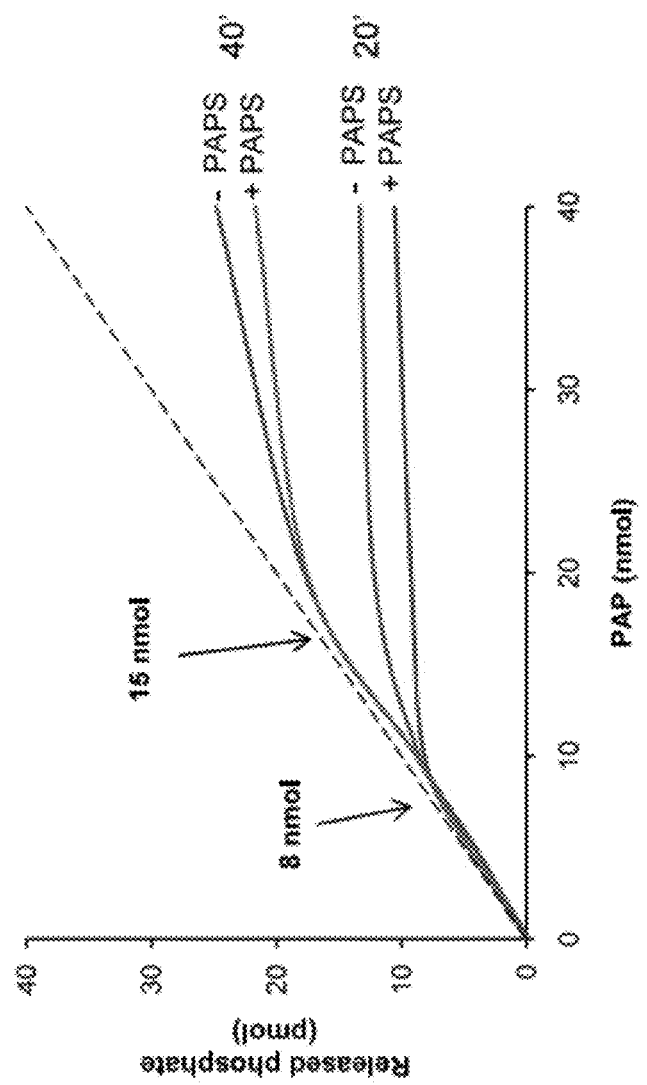
FIG. 7 is a graph of phosphate released from PAP by gPAPP in the presence or absence of PAPS versus PAP concentration.

In this example, the coupling capacity of gPAPP was determined. The coupling capacity of a coupling enzyme is the amount of product that can be completely converted into signal by one μg of the enzyme under specific conditions. In this example, the coupling capacity is the amount of PAP (product) that can be converted by gPAPP into signal (phosphate). The coupling capacity of gPAPP was determined by combining 1 μg gPAPP with increasing amounts of PAP, in the presence or absence of 0.5 mM PAPS in 50 μL assay buffer containing 10 mM $Mg^{2+}$ at pH 7.5 for either 20 or 40 minutes. The released phosphate was then plotted versus PAP input as shown in FIG. 7. It was found that 1 μg PAPP was able to complete the hydrolysis of 8 nmol and 15 nmol of PAP in 20 and 40 minutes, respectively. The coupling capacity for gPAPP was therefore 8 nmol in a 20 minute reaction and 15 nmol in a 40 minute reaction. The presence of PAPS did cause about a 20% inhibition of the hydrolysis when the amount of PAP was greater than the coupling capacity, but PAPS did not change the coupling capacity significantly, as the PAP-hydrolysis curve in the presence of PAPS almost overlaps with the PAP-hydrolysis curve in the absence of PAPS, when PAP concentration is below the coupling capacity.

Example 5

In this example, p-nitrophonol (pNP) was used as a substrate. The sulfotransferase SULT1A1 is known to have a high affinity for pNP, with a half maximal velocity (Km) reported below 1 μM. Measuring the Km of SULT1A1 for pNP therefore requires a highly sensitive test. Because of this, CD73 was used in the reaction in addition to gPAPP, to increase the assay sensitivity.

Figure 8:
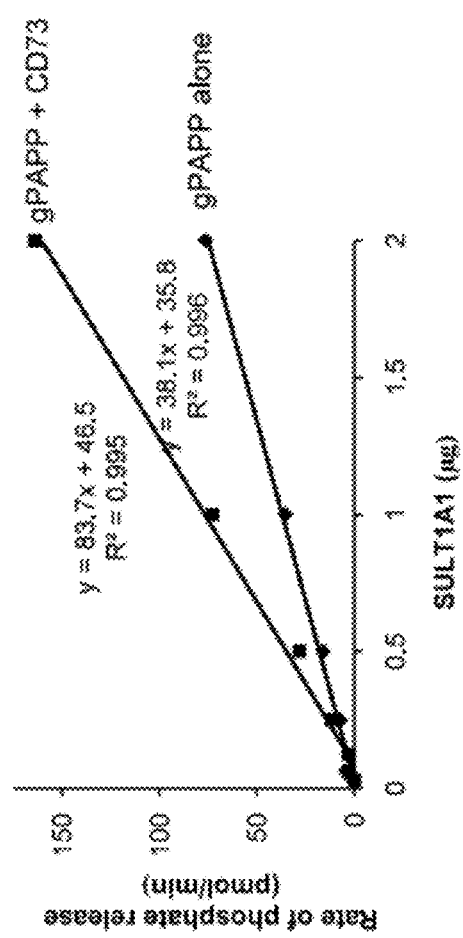
FIG. 8 is a graph of the rate of phosphate release versus SULT1A1 concentration under various conditions.

A series of reactions was performed by combining various amounts of SULT1A1 with 0.25 mM PAPS and 0.25 mM pNP and with either 1 μg gPAPP alone, or both 1 μg gPAPP and 0.1 μg CD73 in 50 μL of Tris buffer containing 10 mM of $MgCl_2$ at pH 7.5. The rate of phosphate release was then plotted versus the enzyme input as shown in FIG. 8. While the rate of phosphate release when coupled to gPAPP alone was 38.1 pmol/min/μg, the rate increased to approximately two fold to 83.7 pmol/min/μg when coupled to both gPAPP and CD73. Since gPAPP and CD73 together release two equivalents of phosphate from each PAP, the specific activity of SULT1A1 was averaged to 40.0±1.9 pmol/min/μg. This specific activity is consistent with the known results obtained using radioisotope assays.

Example 6

Figure 9:
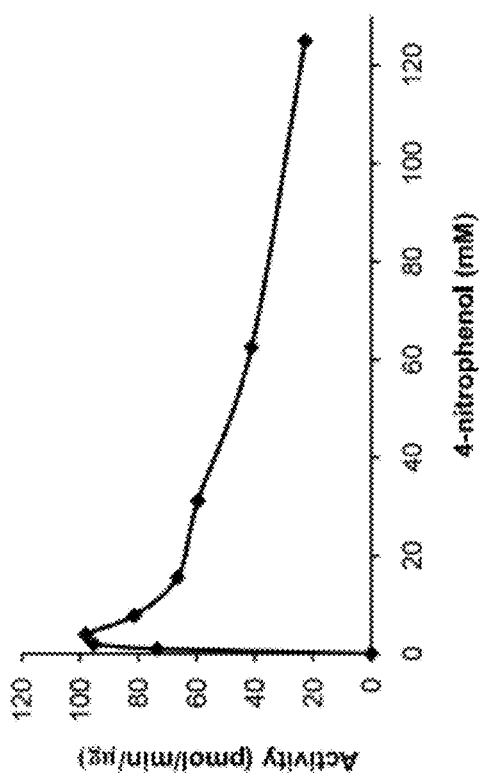
FIG. 9 is a graph of the activity of SULT1A1 versus concentration of pNP.

A series of reactions were performed by combining increasing concentrations of pNP with 0.1 μg SULT1A1, 2 μg PAPP and 0.1 μg CD73 in 200 μL of an assay buffer containing 0.25 mM PAPS, 10 mM $MgCl_2$ at pH 7.5. The free phosphate was measured and the reaction velocity was plotted against pNP concentration as shown in FIG. 9. At pNP concentrations above 4 mM, substrate inhibition was present and the concentration for half maximum velocity was projected to be <1.0 μM of pNP. These values are consistent with reported values for SULT1A1 determined using radioisotope assays in the literature.

Example 7

Figure 10:
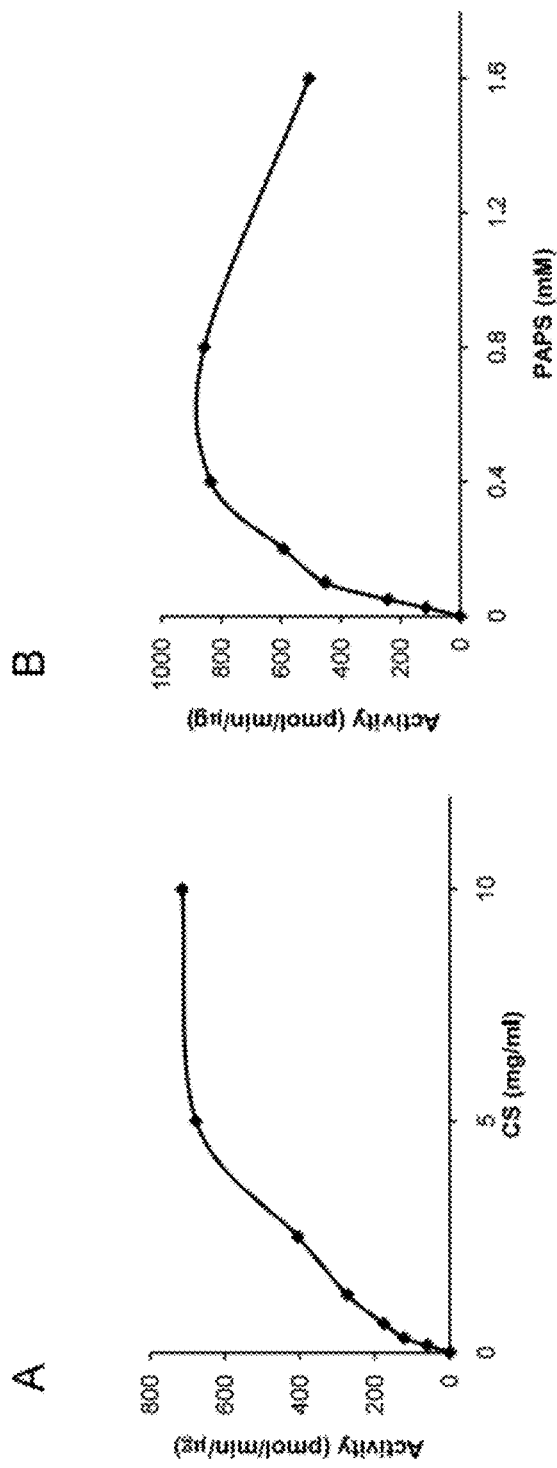
FIG. 10A is a graph of activity of CHST3 versus concentration of CS.
FIG. 10B is a graph of activity of CHST3 versus concentration of PAPS.

Carbohydrate sulfotransferase 3 (CHST3) is a sulfotransferase which is known to catalyze the sulfation of N-acetyl-galactosamine at the 6-O position. In a first series of reactions, 1 μg CHST3 was combined with 1 μg gPAPP and increasing concentrations of CS in 50 μl assay buffer containing 0.8 mM PAPS, 10 mM $MgCl_2$ at pH 7.5. In a second series of reactions, 0.4 μg CHST3 was combined with 1 μg gPAPP and increasing concentrations of PAPS in 50 μL assay buffer containing 0.8 mM PAPS, 10 mg/ml CS, 10 mM $MgCl_2$ at pH 7.5. Under the conditions of the first series of reactions, it was determined that the concentration of CS that lead to a half-maximal velocity (Km for CS) was about 2 mg/ml, as shown in FIG. 10A. Under the conditions of the second series of reactions, the PAPS concentration for half-maximal velocity (Km for PAPS) was below 0.1 mM, as shown in FIG. 10B. It can be seen that substrate inhibition occurred at PAPS levels above 0.5 mM in FIG. 10B, while no substrate inhibition is seen in FIG. 10A.

Example 8

Figure 11:
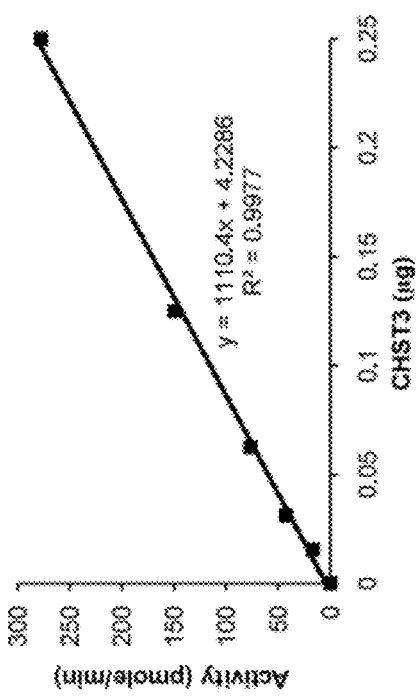
FIG. 11 is a graph of CHST3 activity versus CHST3 concentration.

First, the optimal concentration for CS was visually determined to be >5 mg/ml and the optimal concentration for PAPS was visually determined to be about 0.5 mM using FIGS. 10A and 10B by finding the substrate concentration corresponding to the highest point in the curves. An enzyme dose curve was then created for CHST3 at the optimal concentrations for both the donor and acceptor substrates in FIG. 11. To create the dose curve, 1 μg gPAPP was combined with increasing amounts of CHST3 in the presence of 10 mg/ml of CS and 0.5 mM of PAPS in 50 μl assay buffer containing 10 mM $MgCl_2$ at pH 7.5. The specific activity was determined to be 1110 pmol/min/μg, as shown in FIG. 11, which is consistent with data previously obtained using a gel electrophoresis based radioisotope assay.

In the foregoing detailed description, the invention has been described with reference to specific embodiments. However, it may be appreciated that various modifications and changes can be made without departing from the scope of the invention as set forth.

Embodiments of the invention includes various aspects, some of which are described in the numbered paragraphs below.

1. An assay for detecting activity of a test sulfotransferase comprising: gPAPP and a free phosphate detector. The free phosphate detector may be a colorimetric assay, such as a free phosphate detector including a first reagent and a second reagent, wherein the first reagent comprises ammonium molybdate and the second reagent comprises malachite green oxalate. The assay may further include a source of free phosphate for use as a phosphate standard and/or PAPS and/or PAP. The assay may further include a buffer, which may include magnesium.

2. An assay for detecting activity of a test sulfotransferase comprising: gPAPP and a control sulfotransferase. The control sulfotransferase may be SULT1C4 or CHST3, for example. The assay may further include a source of free phosphate for use as a phosphate standard and/or PAPS and/or PAP. The assay may further include a buffer, which may include magnesium.

3. An assay for detecting activity of a test sulfotransferase comprising: gPAPP; a control sulfotransferase; and a free phosphate detector. The free phosphate detector may be a colorimetric assay, such as a free phosphate detector including a first reagent and a second reagent, wherein the first reagent comprises ammonium molybdate and the second reagent comprises malachite green oxalate. The control sulfotransferase may be SULT1C4 or CHST3, for example. The assay may further include a source of free phosphate for use as a phosphate standard and/or PAPS and/or PAP. The assay may further include a buffer, which may include magnesium.

4. An assay for detecting activity of a test sulfotransferase comprising: gPAPP; a 5' nucleotidase; and a free phosphate detector. The assay may further include PAPS and/or PAP.

An assay for detecting activity of a test sulfotransferase comprising: gPAPP; a 5' nucleotidase; and a control sulfotransferase. The assay may further include PAPS and/or PAP.

An assay for detecting activity of a test sulfotransferase comprising: gPAPP; a 5' nucleotidase; a control sulfotransferase, and a free phosphate detector. The assay may further include PAPS and/or PAP.

5. An assay for detecting activity of a test sulfotransferase comprising: gPAPP, a control sulfotransferase, a free phosphate detector, PAPS and a buffer. The assay may further include PAP and/or a 5' nucleotidase.

6. A method of detecting sulfotransferase activity comprising conducting a first reaction comprising: combining a sulfotransferase, gPAPP, a substrate of the sulfotransferase, and PAPS under conditions to produce PAP; and measuring free phosphate. The first reaction can further include a buffer, which may include magnesium. Measuring free phosphate includes applying a colorimetric assay to the first reaction and measuring optical density.

7. A method of detecting sulfotransferase activity comprising conducting a first reaction comprising: combining a sulfotransferase, gPAPP, a substrate of the sulfotransferase, and PAPS under conditions to produce PAP; measuring free phosphate; and calculating sulfotransferase activity using the measured amount of free phosphate. The first reaction can further include a buffer, which may include magnesium. Measuring free phosphate includes applying a colorimetric assay to the first reaction and measuring optical density.

8. A method of detecting sulfotransferase activity comprising conducting a first reaction and a second reaction. The first reaction comprises combining a sulfotransferase, gPAPP, a substrate of the sulfotransferase, and PAPS under conditions to produce PAP; and measuring free phosphate. Measuring free phosphate includes applying a colorimetric assay to the first reaction and measuring optical density. The first reaction can further include a buffer, which may include magnesium. The second reaction comprises combining the substrate of the sulfotransferase and the PAPS with the phosphatase in the absence of the sulfotransferase and measuring free phosphate, such as under the same conditions as the first reaction (except for the absence of sulfotransferase), wherein the second reaction provides a background control for the first reaction. The second reaction can include the same buffer as the first reaction. The method can further include reducing the measured phosphate of the first reaction by the measured phosphate of the second reaction to calculate the amount of phosphate correlated to the sulfotransferase reaction.

9. A method of detecting sulfotransferase activity comprising conducting a first reaction comprising: combining a sulfotransferase, gPAPP, 5'-nucleotidase, a substrate of the sulfotransferase, and PAPS under conditions to produce PAP; and measuring free phosphate. Measuring free phosphate includes applying a colorimetric assay to the first reaction and measuring optical density.

10. A method of testing an agent for effect upon a sulfotransferase comprising: combining a sulfotransferase, gPAPP, a substrate of the sulfotransferase, the agent and PAPS under conditions to produce PAP; measuring free phosphate; and calculating sulfotransferase activity using the measured amount of free phosphate. The reaction can further include a buffer, which may include magnesium. Measuring free phosphate includes applying a colorimetric assay to the first reaction and measuring optical density. The method can further include performing the same reaction in the absence of the agent, and comparing the results of the two reactions to determine the effect of the agent upon sulfotransferase activity.

The invention claimed is:

1. A method of detecting sulfotransferase activity comprising:
   conducting a reaction comprising combining a sulfotransferase, Golgi-resident PAP-phosphatase (gPAPP), a substrate of the sulfotransferase, and 3'-phosphoadenosine-5'-phosphosulfate (PAPS) under conditions to produce 3'-phosphoadenosine-5'-phosphate (PAP); and
   measuring free phosphate; and
   comparing the measured free phosphate to a free phosphate standard curve or equation or to a free phosphate level obtained in a separate reaction.

2. The method of claim 1 further comprising calculating sulfotransferase activity using the measured amount of free phosphate.

3. The method of claim 1 wherein measuring the free phosphate comprises measuring optical density.

4. The method of claim 1 further comprising conducting a separate reaction comprising combining the substrate of the sulfotransferase and PAPS with the phosphatase in the absence of the sulfotransferase and measuring free phosphate, wherein the separate reaction provides a background control.

5. The method of claim 4 further comprising reducing the measured phosphate of the reaction by the measured phosphate of the separate reaction to calculate the amount of phosphate correlated to the sulfotransferase reaction.

6. The method of claim 1 wherein measuring free phosphate comprises applying a colorimetric free phosphate detection assay to the first reaction.

7. The method of claim 1 wherein measuring free phosphate comprises adding a first reagent to the reaction comprising ammonium molybdate and then adding a second reagent to the reaction comprising malachite green oxalate.

8. The method of claim 1 wherein the separate reaction comprises a background control reaction wherein the Golgi-resident PAP-phosphatase (gPAPP), the substrate of the sulfotransferase, and the 3'-phosphoadenosine-5'-phosphosulfate (PAPS) where combined without the sulfotransferase.

9. The method of claim 1 wherein the separate reaction comprises a reaction wherein the sulfotransferase, the Golgi-resident PAP-phosphatase (gPAPP), the substrate of the sulfotransferase, and the 3'-phosphoadenosine-5'-phosphosulfate (PAPS) were combined and wherein one or more conditions were different from those of the reaction.

* * * * *